(12) United States Patent
Sonnenborg et al.

(10) Patent No.: US 11,096,553 B2
(45) Date of Patent: Aug. 24, 2021

(54) METHOD FOR PROCESSING IMAGE DATA USING A NON-LINEAR SCALING MODEL AND A MEDICAL VISUAL AID SYSTEM

(71) Applicant: AMBU A/S, Ballerup (DK)

(72) Inventors: Finn Sonnenborg, Frederikssund (DK); Brian Nielsen, Næstved (DK); Curt Allan Johansson, Lund (SE); Sebastian Ortega Zafra, Malmö (SE); Qian Yang, Lund (SE); Kai-Cheng Chan, New Yaipei (TW); Wang Chang-Yu, New Taipei (TW)

(73) Assignee: AMBU A/S, Ballerup (DK)

( * ) Notice: Subject to any disclaimer, the term of this patent is extended or adjusted under 35 U.S.C. 154(b) by 75 days.

(21) Appl. No.: 16/620,320

(22) PCT Filed: Jun. 19, 2018

(86) PCT No.: PCT/EP2018/066246
§ 371 (c)(1),
(2) Date: Dec. 6, 2019

(87) PCT Pub. No.: WO2018/234305
PCT Pub. Date: Dec. 27, 2018

(65) Prior Publication Data
US 2020/0405124 A1 Dec. 31, 2020

(30) Foreign Application Priority Data
Jun. 19, 2017 (EP) ..................................... 17176592

(51) Int. Cl.
*G06T 5/00* (2006.01)
*A61B 1/00* (2006.01)
(Continued)

(52) U.S. Cl.
CPC ...... *A61B 1/00009* (2013.01); *A61B 1/00045* (2013.01); *A61B 1/0684* (2013.01);
(Continued)

(58) Field of Classification Search
CPC . A61B 1/0009; A61B 1/00045; A61B 1/0684; A61B 1/00103; A61B 1/00057;
(Continued)

(56) References Cited

U.S. PATENT DOCUMENTS

| 4,774,565 A | 9/1988 | Freeman |
| 5,652,621 A | 7/1997 | Adams |

(Continued)

FOREIGN PATENT DOCUMENTS

| EP | 2690868 | 1/2014 |
| JP | H04197331 | 7/1992 |

(Continued)

OTHER PUBLICATIONS

Ozbek, Onur, Improving DAC Integral Nonlinearity (INL) through Gain Correction, Oct. 2011, Planet Analog, 1-6. (Year: 2011).*
(Continued)

*Primary Examiner* — Matthew C Bella
*Assistant Examiner* — Kathleen M Broughton
(74) *Attorney, Agent, or Firm* — Faegre Drinker Biddle & Reath LLP

(57) ABSTRACT

A method for obtaining and processing image data by using a medical visual aid system including a monitor and an endoscope configured to be inserted into a body cavity and having an image capturing device and a light emitting device, the method including illuminating a field of view of the image capturing device with the light emitting device, capturing the image data using the image capturing device, providing a non-linear scaling model adapted to the body cavity, adjusting the image data by applying the non-linear
(Continued)

scaling model such that adjusted image data is formed, and presenting the adjusted image data on the monitor.

26 Claims, 5 Drawing Sheets

(51) Int. Cl.
*A61B 1/06* (2006.01)
*G06T 5/20* (2006.01)

(52) U.S. Cl.
CPC .............. *G06T 5/007* (2013.01); *G06T 5/009* (2013.01); *G06T 5/20* (2013.01); *G06T 2207/10068* (2013.01)

(58) Field of Classification Search
CPC ........... G06T 5/20; G06T 5/009; G06T 5/007; G06T 2207/10068; H04N 5/2256; H04N 5/23229; H04N 5/23293; H04N 5/2354
See application file for complete search history.

(56) References Cited

U.S. PATENT DOCUMENTS

| | | | |
|---|---|---|---|
| 6,441,845 B1 | 8/2002 | Kanichi | |
| 6,734,894 B1 | 5/2004 | Higuchi | |
| 6,760,485 B1 | 7/2004 | Gilman | |
| 7,450,151 B2 | 11/2008 | Kaneko | |
| 7,502,505 B2 | 3/2009 | Malvar | |
| 8,023,763 B2 | 9/2011 | Kwon | |
| 8,472,749 B2 | 6/2013 | Watanabe | |
| 8,638,995 B2 | 1/2014 | Greenstein | |
| 9,119,553 B2 | 9/2015 | Ishihara | |
| 9,179,831 B2 | 11/2015 | McGrail et al. | |
| 9,182,347 B2 | 11/2015 | Ishihara | |
| 9,220,400 B2 | 12/2015 | Petersen | |
| 9,241,139 B2 | 1/2016 | Ishihara | |
| 9,345,392 B2 | 5/2016 | Saito | |
| 9,968,241 B2 | 5/2018 | Iuel | |
| 10,321,804 B2 | 6/2019 | Jacobsen et al. | |
| 10,624,531 B2 | 4/2020 | Matthison-Hansen | |
| 10,624,617 B2 | 4/2020 | Matthison-Hansen et al. | |
| 10,964,844 B2 | 3/2021 | Lutgen | |
| 2003/0007672 A1 | 1/2003 | Harman | |
| 2005/0206636 A1 | 9/2005 | Kanai | |
| 2006/0241418 A1 | 10/2006 | Abe | |
| 2011/0164127 A1 | 7/2011 | Stehle | |
| 2011/0306831 A1 | 12/2011 | Kohnke et al. | |
| 2012/0041533 A1 | 2/2012 | Bertolino et al. | |
| 2012/0105612 A1 | 5/2012 | Yoshino | |
| 2013/0041214 A1 | 2/2013 | Maahs et al. | |
| 2013/0245411 A1 | 9/2013 | Saito | |
| 2014/0015946 A1 | 1/2014 | Yamagidate | |
| 2014/0128012 A1 | 1/2014 | Zhou | |
| 2014/0088497 A1 | 3/2014 | Campbell | |
| 2014/0275764 A1 | 9/2014 | Shen | |
| 2014/0316197 A1* | 10/2014 | St. George | A61B 1/00036 600/109 |
| 2015/0049177 A1 | 2/2015 | Johansson | |
| 2016/0143520 A1 | 5/2016 | Masaki | |
| 2017/0032502 A1 | 2/2017 | Hemert | |
| 2017/0042411 A1 | 2/2017 | Kang et al. | |
| 2017/0280793 A1 | 10/2017 | Hatano | |
| 2018/0207403 A1 | 7/2018 | Wang | |
| 2019/0053690 A1 | 2/2019 | Suzuki et al. | |
| 2019/0254503 A1 | 8/2019 | Hatano et al. | |

FOREIGN PATENT DOCUMENTS

| | | |
|---|---|---|
| JP | 3442653 B2 * | 9/2003 |
| JP | 4448277 B2 * | 4/2010 |
| WO | WO2014/0106511 | 7/2014 |
| WO | WO2015/106955 A1 | 7/2015 |

OTHER PUBLICATIONS

Kim, Eun-Su et al, Optimal Piece Linear Segments of Gamma Correction for CMOS Image Sensors, Nov. 2005, IEICE Trans. Electron., vol. E88-C, No. 11 2090-2093. (Year: 2005).*
International Search Report and Written Opinion from corresponding Application No. PCT/EP2018/066246, dated Aug. 28, 2018.
Extended European Search Report from corresponding Application No. EP 17176592.8, dated Dec. 15, 2017.

* cited by examiner

METHOD FOR PROCESSING IMAGE DATA USING A NON-LINEAR SCALING MODEL AND A MEDICAL VISUAL AID SYSTEM

CROSS-REFERENCE TO RELATED APPLICATIONS

This application is a National stage application filed under 35 U.S.C. § 371 of International Application No. PCT/EP2018/066246, filed on Jun. 19, 2018, which claims the benefit of European Patent Application No. 17176592.8, filed on Jun. 19, 2017, which applications are incorporated herein by reference in their entirety.

TECHNICAL FIELD

The present invention relates to endoscopes. More particularly, it is related to a method for obtaining and processing image data, a medical visual aid system, an endoscope forming part of the medical visual aid system and a monitor forming part of the visual aid system.

BACKGROUND

Endoscopes are well known devices for visually inspecting inaccessible places such as human body cavities. Typically, the endoscope comprises an elongated insertion tube with a handle at the proximal end as seen from the operator and visual inspections means, such as a built in camera with an image sensor and a light source at the distal end of the elongated insertion tube. The endoscopes are typically connected to monitors in order to display images captured by the camera while inserted into an object to be observed. Electrical wiring for the camera and the light source such as a LED run along the inside of the elongated insertion tube from the handle to the tip at the distal end. Instead of a LED endoscopes may also be fibre-optic, in which case the optical fibres run along the inside of the elongated insertion tube.

In order to be able to manoeuvre the endoscope inside the body cavity, the distal end of the endoscope may comprise a section with increased flexibility, e.g. an articulated tip part allowing the operator to bend this section. Typically this is done by tensioning or slacking pull wires also running along the inside of the elongated insertion tube from the articulated tip part to a control mechanism of the handle. Furthermore, a working channel may run along the inside of the insertion tube from the handle to the tip, e.g. allowing liquid to be removed from the body cavity or allowing the insertion of surgical instruments or the like into the body cavity.

In order to reduce the risk of cross-contamination and avoid the cumbersome procedure of cleaning endoscopes after use, it is desirable to provide endoscopes that are designed for single-use. In order to keep costs at a low level single-use endoscopes are often designed with as few as possible components. However, it is still desirable to obtain the best possible image to be displayed on the screen. In complex reusable endoscopes one way of ensuring the image quality is achieved by providing a light source that adequately illuminates the object to be observed and the light intensity from the light source may even be automatically adjusted by analysing images captured by the camera. In single-use endoscopes it is desirable with a simple light source such as an LED, which may be disposed at the distal tip without any optical components such as lenses, light guides or light reflecting elements to focus, shape or distribute the light emitted from the LED. An example of such configuration is known from WO14106511.

While this configuration is desirable due to the simple design, the light source may course parts of the object to be observed to be over-exposed causing pixels of the image sensor to be saturated so that information about the observed object is lost. As a result images displayed on the monitor will in some areas appear too bright and other areas will appear too dark in order to derive the desired information about the object to be observed. This is especially the case when the endoscope is inserted into a tubular structure such as lungs of human beings.

With a view to this, the objective is to provide a method and an endoscope system that in a simple and cost efficient way improves the image quality.

SUMMARY

Accordingly, the present invention preferably seeks to mitigate, alleviate or eliminate one or more of the above-identified deficiencies in the art and disadvantages singly or in any combination and solves at least the above mentioned problems e.g. by providing according to a first aspect a method for processing image data obtained using a medical visual aid system comprising an endoscope and a monitor, wherein the endoscope is configured to be inserted into a body cavity and comprises an image capturing device for capturing image data and a light emitting device, said method comprising providing a non-linear scaling model adapted to the body cavity, adjusting the image data by applying the non-linear scaling model such that adjusted image data is formed, presenting the adjusted image data on the monitor An advantage is that by using the non-linear scaling model and having this adapted to the body cavity, images, based on the adjusted image data, presented on the monitor can easily and quickly be analyzed by an operator, which in turn implies improved health care.

The method may further comprise applying exposure settings of the image capturing device, such that no regions of the image covering more than two neighboring pixels, preferably more than a single pixel, are saturated by light.

An advantage is that information will not be lost in overexposed areas of the image. The darkest areas of the image, may become even darker, but the information will still be in the pixels. Information in the darkest area will be made visible to the user by application of the non-linear scaling model.

The method may further comprise applying exposure settings emphasizing on a central part of the field of view of the image capturing device.

An advantage is, in case of examining a tube-formed cavity, that by emphasizing on the central part the image data reflecting this part will comprise additional information, which in turn implies that a result of a refinement of the image data, e.g. by using the non-linear scaling model, can be done at a later stage such that additional details are made visible to the operator.

The non-linear scaling model may also be adapted to the monitor.

Different monitors may handle image data differently, and thereby by knowing which kind of monitor that is being used the non-linear scaling model can be adapted accordingly, which in turn results in that images presented on the monitor can easily be analyzed by the operator.

The non-linear scaling model may also be adapted to the light emitting device.

Different light emitting devices may enlighten the body cavity differently. Thus, by knowing which type of light emitting devices that are being used by the endoscope the non-linear scaling model can be adapted, which in turn results in that images presented on the monitor can easily be analyzed by the operator.

The non-linear scaling model may be a non-linear intensity scaling model, such as a non-linear gamma correction model.

The non-linear intensity scaling model may be configured to, in the image displayed on the monitor, increase the contrast in the dark parts of the image and reduce the contrast in the parts of the image having an intermediate light intensity in a manner whereby pixels having low pixel intensity values are scaled up significantly and pixels having mid-range pixel intensity values are only slightly adjusted or not adjusted at all.

Thus, the non-linear scaling model may provide a lower average gain to the pixels having mid-range pixel intensity values than the average gain provided by a standard gamma function, providing the same average gain to the pixels having low pixel intensity values as the non-linear scaling mode. The standard gamma function is defined as:

$$V_{out}=V_{in}^{\gamma}$$

An advantage of this is that it may look like as if a light source illuminates both the regions close to the endoscope tip and the regions further away from the endoscope tip with the same light intensity.

The dark part of the image may be defined as the parts of the image having intensities between 0% and 7% of the maximum intensity. The parts of the image having an intermediate light intensity may be defined as the parts of the image having intensities between 8% and 30% of the maximum intensity.

The non-linear intensity scaling model may be a scaling function mapping input intensities to output intensities.

The scaling function may be provided with a bend, i.e. the slope of the scaling function may be neither continuously increasing or continuously decreasing. In some embodiments the scaling function has a first part, the first part being followed by a second part, the second part being followed by a third part, and wherein the average slope of the second part is lower than the average slope of the first part and the average slope of the third part.

This allows a high gain to be provided to the dark parts of the image, a lower gain to be provided to the parts of the image having an intermediate light intensity, while at the same time utilizing the full dynamic range of the monitor.

The step of adjusting the image data by applying the non-linear intensity scaling model such that adjusted image data is formed may further comprise increasing intensity of a low intensity image data sub-set, wherein the low intensity image data sub-set comprises the image data having intensity levels up to 25% of maximum intensity, and decreasing intensity of a high intensity image data sub-set, wherein the high intensity image data sub-set comprises the image data having intensity levels from 95% of the maximum intensity.

An advantage with this is that the adjusted image data that represents faraway lying (in relation to the image capturing device) areas of the body can easily be analyzed by the operator.

The non-linear scaling model may be set to increase intensity of the low intensity image data sub-set by a first increase factor, wherein the first increase factor is greater than intensity factors used for other sub-sets of the image data.

An advantage of increasing the intensity of the low image intensity image data sub-set to a higher extent than in the rest of the image data, is that faraway lying areas of the body cavity can easily be analyzed by the operator.

The step of providing a non-linear scaling model adapted to the body cavity may further comprise determining a body cavity type to which the body cavity is related, and selecting the non-linear scaling model based on the body cavity type.

An advantage of this is that differences in terms of shape and light reflecting properties of different body cavities can be taken into account, which in turn provides for that the non-linear scaling model may be customized for different body cavities, which in turn can make it possible to provide images that can easily be analyzed via the monitor for a wide range of different body cavities.

In some embodiments the non-linear scaling model used for adjusting the image data is select from a set of non-linear scaling models comprising a first non-linear scaling model and a second non-linear scaling model.

In some embodiments the set comprises at least 3, at least 4 or at least 5 non-linear scaling models.

In some embodiments the first non-linear scaling model and the second non-linear scaling model both are adapted to the same monitor.

In some embodiments the image data is obtained using a single use endoscope, and wherein the monitor adjusts the image data by applying the non-linear scaling model.

In some embodiments the first non-linear scaling model and the second non-linear scaling model are stored in the monitor.

According to a second aspect, a medical visual aid system comprising an endoscope and a monitor is provided, wherein the endoscope is configured to be inserted into a body cavity and comprises an image capturing device and a light emitting device, and the monitor comprises an image data processing device for adjusting the image data by applying a non-linear scaling model adapted to the body cavity such that adjusted image data is formed, and a display device for presenting the adjusted image data.

An advantage is that by using the non-linear scaling model and having this adapted to the body cavity, images, based on the adjusted image data, presented on the monitor can easily and quickly be analyzed by an operator, which in turn implies improved health care.

Further, exposure settings of the image data processing device may be configured to emphasize on a central part of the field of view of the image capturing device.

An advantage is, in case of examining a tube-formed cavity, that by emphasizing on the central part the image data reflecting this part will comprise additional information, which in turn implies that a result of a refinement of the image data, e.g. by using the non-linear scaling model, can be done at a later stage such that additional details are made visible to the operator.

The non-linear scaling model may also be adapted to the display device set as a recipient of the adjusted image data.

Different monitors may handle image data differently, and thereby by knowing which kind of monitor that is being used the non-scaling model can be adapted accordingly, which in turn results in that images presented on the monitor can easily be analyzed by the operator.

The non-linear scaling model may also be adapted to the light emitting device.

Different light emitting devices may enlighten the body cavity differently. Thus, by knowing which type of light emitting devices that are being used by the endoscope the non-scaling model can be adapted, which in turn results in that images presented on the monitor can easily be analyzed by the operator.

The non-linear scaling model may be a non-linear intensity scaling model, such as a non-linear gamma correction model.

The non-linear intensity scaling model may be configured to, in the image displayed on the monitor, increase the contrast in the dark parts of the image and reduce the contrast in the parts of the image having an intermediate light intensity in a manner whereby pixels having low pixel intensity values are scaled up significantly and pixels having mid-range pixel intensity values are only slightly adjusted or not adjusted at all.

Thus, the non-linear scaling model may provide a lower average gain to the pixels having mid-range pixel intensity values than the average gain provided by a standard gamma function, providing the same average gain to the pixels having low pixel intensity values as the non-linear scaling mode. The standard gamma function is defined as:

$$V_{out} = V_{in}^{\gamma}$$

An advantage of this is that it may look like as if a light source illuminates both the regions close to the endoscope tip and the regions further away from the endoscope tip with the same light intensity.

The dark part of the image may be defined as the parts of the image having intensities between 0% and 7% of the maximum intensity. The parts of the image having an intermediate light intensity may be defined as the parts of the image having intensities between 8% and 30% of the maximum intensity.

The non-linear intensity scaling model may be a scaling function mapping input intensities to output intensities.

The scaling function may be provided with a bend, i.e. the slope of the scaling function may be neither continuously increasing or continuously decreasing. In some embodiments the scaling function has a first part, the first part being followed by a second part, the second part being followed by a third part, and wherein the average slope of the second part is lower than the average slope of the first part and the average slope of the third part. This allows a high gain to be provided to the dark parts of the image, a lower gain to be provided to the parts of the image having an intermediate light intensity, while at the same time utilizing the full dynamic range of the monitor.

The image data processing device for adjusting the image data by applying a non-linear scaling model may be configured to increase intensity of a low intensity image data sub-set, wherein the low intensity image data sub-set comprises intensity levels up to 25% of maximum intensity, and decrease intensity of a high intensity image data sub-set, wherein the high intensity image data sub-set comprises intensity levels from 95% of the maximum intensity.

An advantage with this is that the adjusted image data that represents faraway lying (in relation to the image capturing device) areas of the body can easily be analyzed by the operator.

The non-linear scaling model may be set to increase intensity of the low intensity image data sub-set by a first increase factor, wherein the first increase factor is greater than intensity factors used for other sub-sets of the image data.

An advantage of increasing the intensity of the low image intensity image data sub-set to a higher extent than in the rest of the image data is that faraway lying areas of the body cavity can easily be analyzed by the operator.

The image data processing device may further be configured to determine a body cavity type to which the body cavity is related, and select the non-linear scaling model based on the body cavity type.

An advantage of this is that differences in terms of shape and light reflecting properties of different body cavities can be taken into account, which in turn provides for that the non-linear scaling model may be customized for different body cavities, which in turn can make it possible to provide images that can easily be analyzed via the monitor for a wide range of different body cavities.

In some embodiments the non-linear scaling model used for adjusting the image data is select from a set of non-linear scaling models comprising a first non-linear scaling model and a second non-linear scaling model.

In some embodiments the first non-linear scaling model and the second non-linear scaling model both are adapted to the display device.

In some embodiments the image data is obtained using a single use endoscope.

In some embodiments the first non-linear scaling model and the second non-linear scaling model are stored in the monitor.

According to a third aspect, an endoscope configured to be inserted into a body cavity is provided. This endoscope comprises an image capturing device and a light emitting device, and forms part of the medical visual aid system according to the second aspect.

According to a fourth aspect it is provided a monitor comprising an image data processing device for adjusting image data by applying a non-linear scaling model adapted to a body cavity such that adjusted image data is formed, and a display device for presenting the adjusted image data, and forming part of the visual aid system according to the second aspect.

According to a fifth aspect it is provided a computer program comprising computer program code adapted to perform the method according to the first aspect when said computer program is run on a computer.

According to a sixth aspect is it provided a method for obtaining and presenting image data by using a medical visual aid system comprising an endoscope and a monitor, wherein the endoscope is configured to be inserted into a body cavity and comprises an image capturing device and a light emitting device, said method comprising illuminating a field of view of the image capturing device with the light emitting device, capturing the image data using the image capturing device, providing a non-linear scaling model adapted to the body cavity, adjusting the image data by applying the non-linear scaling model such that adjusted image data is formed, and presenting the adjusted image data on the monitor.

BRIEF DESCRIPTION OF DRAWINGS

The above, as well as additional objects, features and advantages of the present invention, will be better understood through the following illustrative and non-limiting detailed description of preferred embodiments of the present invention, with reference to the appended drawings, wherein.

DETAILED DESCRIPTION

Figure 1:
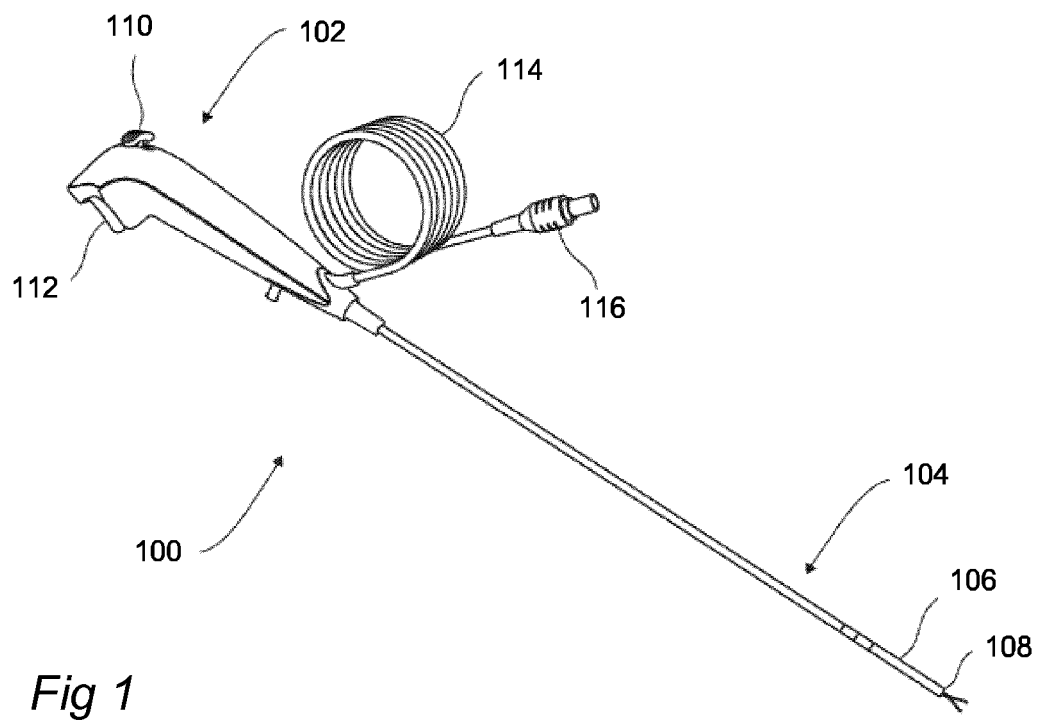
FIG. 1 illustrates an example of an endoscope.

FIG. 1 illustrates an example of an endoscope 100. This endoscope may be adapted for single-use. The endoscope 100 is provided with a handle 102 attached to an insertion tube 104 provided with a bending section 106. The insertion tube 104 as well as the bending section 106 may be provided with one or several working channels such that instruments, such as a gripping device, may be inserted into a human body via the endoscope. One or several exit holes of the one or several channels may be provided in a tip part 108 of the endoscope 100. In addition to the exit holes, a camera sensor, such as a CMOS sensor or any other image capturing device, as well as one or several light sources, such as light emitting diodes (LEDs) or any other light emitting devices, may be placed in the tip part 108. By having the camera sensor and the light sources and a monitor 200, illustrated in FIG. 2, configured to display images based on image data captured by the camera sensor, an operator is able to see and analyze an inside of the human body in order to for instance localize a position for taking a sample. In addition, the operator will be able to control the instrument in a precise manner due to the visual feedback made available by the camera sensor and the monitor. Further, since some diseases or health issues may result in a shift in natural colors or other visual symptoms, the operator is provided with valuable input for making a diagnosis based on the image data provided via the camera sensor and the monitor.

In order to make it possible for the operator to direct the camera sensor such that different field of views can be achieved, the endoscope is comprising a bending section 106 that can be bent in different directions with respect to the insertion tube 104. The bending section 106 may be controlled by the operator by using a knob 110 placed on the handle 102. The handle 102 illustrated in FIG. 1 is designed such that the knob 106 is controlled by a thumb of the operator, but other designs are also possible. In order to control a gripping device or other device provided via a working channel a push button 112 may be used. The handle 102 illustrated in FIG. 1 is designed such that a pointer finger of the operator is used for controlling the gripping device, but other designs are also possible.

Figure 2:
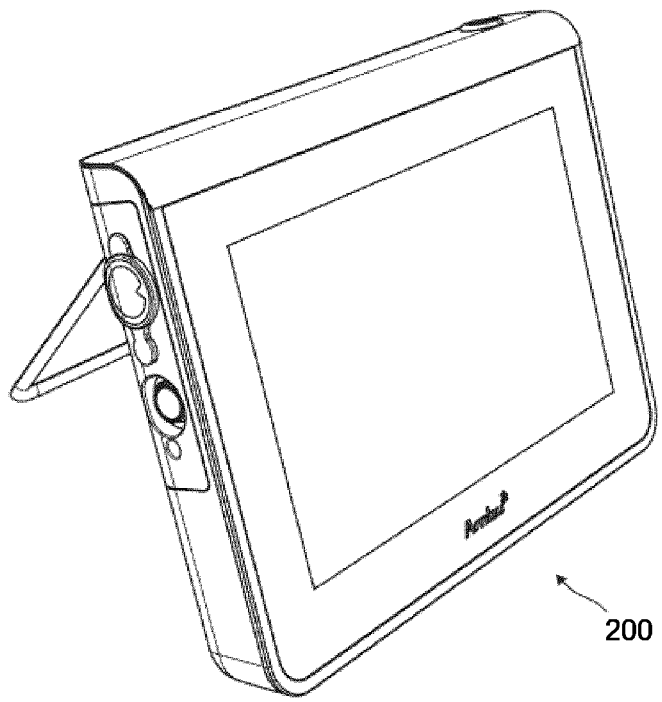
FIG. 2 illustrates an example of a monitor that can be connected to the endoscope illustrated in FIG. 1.

The image data captured by the camera sensor and optionally also other data captured by other sensors placed in the tip part can be transferred via a connection cable 114 and a connector 116 to a monitor 200 illustrated in FIG. 2. Even though wire-based data transmission is illustrated, it is equally possible to transfer image data by using wireless data transmission.

The monitor device 200 is preferably a re-usable piece of equipment. By having one single-use piece of equipment and another re-usable piece of equipment, most of the data processing capability may be placed in the re-usable piece of equipment in order to reach a cost efficient level at the same time as being safe to use from a health perspective.

Data processing operations closely related to e.g. operation of the camera sensor, such as reading out image data, may be performed in the endoscope itself, while more complex data processing operations, requiring more computational power, may be made in the monitor 200. Since most of the more complex data processing operations are related to image data processing an Image Signal Processor (ISP) may be provided in the monitor and used for image data processing operations.

Figure 3:
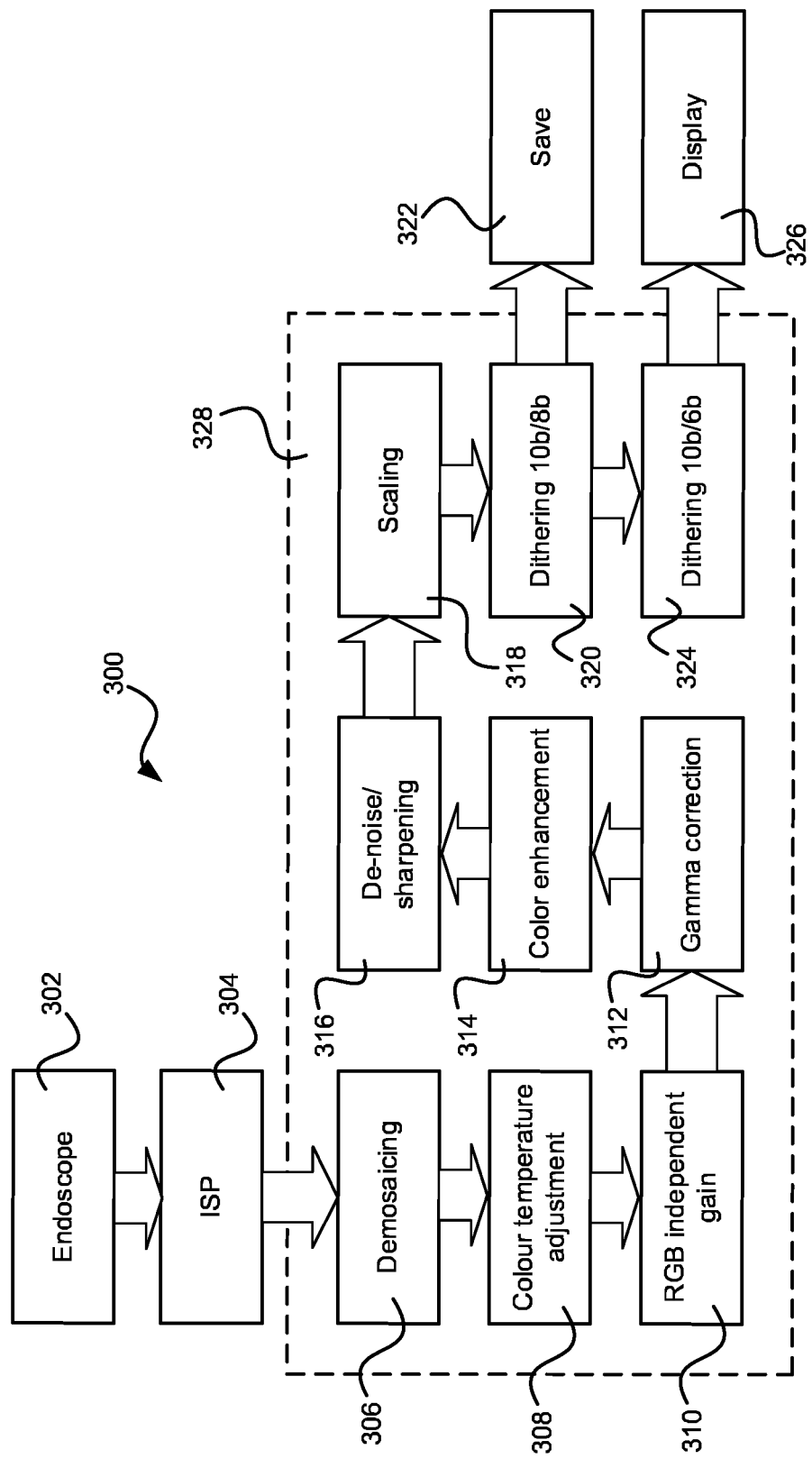
FIG. 3 is a flow chart illustrating a number of steps for processing image data before presenting this to an operator via e.g. the monitor illustrated in FIG. 2.

In order to be able to display an image on the monitor, e.g. an image that is depicting the inside of the body being examined, such that the operator easily can interpret this and make conclusions from it, the image data captured by the image sensor can be processed in a number of steps. Below is given a sequence of steps 300, illustrated in FIG. 3, by way of example that can be made in order to be able to present the image in a way such the operator easily can make use of this.

In a first step 302, the image data comprising pixels, each provided with at least one pixel intensity value, is captured using an endoscope, such as the endoscope illustrated in FIG. 1.

In a second step 304, by using the ISP settings related to for instance exposure may be adjusted in order to provide for that the image data is captured that at a later stage can be refined. If detected that the exposure settings are not adjusted correctly, for instance in that a large portion of the image data is overexposed and/or underexposed, the exposure settings may be changed. This step may be performed in the endoscope.

In a third step 306, the image data can be demosaiced, e.g. conversion from Bayer level color space to RGB color space. For instance, in this step so-called Freeman interpolation (described in U.S. Pat. No. 4,774,565) may be made in order to remove color artifacts in the image data. However, also other algorithms for demosaicing may be applied.

In a fourth step 308, a color temperature adjustment can be made. This adjustment may be based on user input. For instance, the operator may have chosen a color temperature scheme called "warm" comprising warm yellowish colors, and in this step the image data is adapted to comply with this color temperature scheme.

In a fifth step 310, as a complement to or instead of the color temperature adjustment, independent gains may be set for the different color channels, which in most cases are red, green and blue (RGB). This setting of gain may be based on user inputs.

In a sixth step 312, a gamma correction can be made. Gamma correction is in this context to be understood to be how much to increase or decrease pixel intensity values in different spans in order to provide for that details in dark areas, i.e. low pixel intensity values, and light areas, i.e. high pixel intensity values, are made visible to the operator. As will be described in further detail below and further illustrated in FIG. 6, this step may be made by using a non-linear scaling model, e.g. a non-linear gamma correction model. Using the non-linear gamma correction model has the effect that for instance a first pixel having a low pixel intensity value, though above zero, is significantly scaled up, that is, the low pixel intensity value is significantly increased, while a second pixel having mid-range pixel intensity value is only slightly adjusted or not adjusted at all. By using a non-linear scaling model in this way details of underexposed areas may become more easy to analyze for the operator analyzing the image provided via the monitor 200.

The non-linear scaling model may preferably be applied in connection with a controlling of the exposure settings of the image capturing device, such that over exposure, and thereby saturation of pixels, is avoided. If there is an area where the majority of pixels are saturated, information on the actual structure in this area is lost and cannot be regained. Preferably, the exposure settings are selected such that no regions of the image covering more than two neighboring pixels, preferably more than a single pixel, are saturated by light.

Even though illustrated to be performed after the third step 306, the gamma correction may in an alternative embodiment be made before the third step 306 related to demosaicing.

In a seventh step 314, a color enhancement can be made. A consequence of the gamma correction made in the sixth step 312 can be that the image data loses its color intensity. Therefore, by having the color enhancement made after the gamma correction, the color intensity may be adjusted after the gamma correction and hence compensate for effects caused by the gamma correction. The adjustment may be made based on that a saturation gain is made, and how much gain to choose in this step may be based on a gamma level used in the previous step, i.e. which non-linear gamma correction model that was used in the previous step in case several alternatives are available. For instance, if the gamma level used in the previous step provided only a slight deviation from a linear gamma correction model a need for color enhancement may be less compared to if the gamma level used in the previous step significantly deviated from the linear gamma correction model.

In an eighth step 316, a de-noising/sharpening can be made. This step may include both identifying noise caused by temporal effects, spatial effects and signal-level effects, e.g. fixed pattern noise, and then removing this noise.

In a ninth step 318, the image data can be size scaled in order to reach a pre-set size, if different from current size.

In a tenth step 320, the image data can be transformed from one form to another, in this particular example from a 10 bits format to a 8 bits format, before the image data is saved in an eleventh step 322.

In a twelfth step 324, the image data can be transformed from one form to another, in this particular example from a 10 bits format to a 6 bits format, before the image data is displayed in a thirteenth step 326.

The third to tenth step 306-320 and the twelfth step 324 may be made in a so-called FPGA (Field Programmable Gate Array) device provided in the monitor 200.

Even though exemplified in a certain order, different orders are also possible. In addition, one or several steps may be omitted if deemed not necessary for instance based on a quality of the image data and/or requirements of the images displayed on the monitor.

Figure 4:
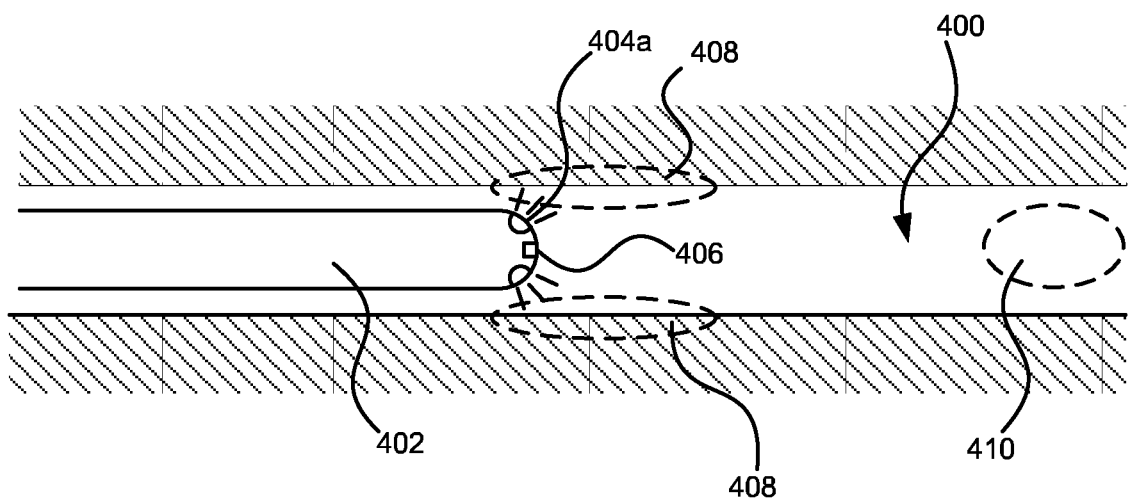
FIG. 4 generally illustrates a tip part of an endoscope placed inside a bronchial tube.

As illustrated in FIG. 4 by way of example, when examining a bronchial tube 400 using an endoscope 402, similar to the endoscope 100 illustrated in FIG. 1, light sources 404a, 404b placed next to a camera sensor 406 may result in that a close lying first area 408 of the bronchial tube is lightened up significantly by the light sources 404a, 404b, while a faraway lying second area 410 due to the tube-shaped form of the bronchial tube may not be lightened up at all, or at least less than the first area, by the light sources 404a, 404b. Thus, due to the tube-shaped form of the bronchial tube the first area 408 is likely to be overexposed while the second area 410 is likely to be underexposed.

Figure 5:
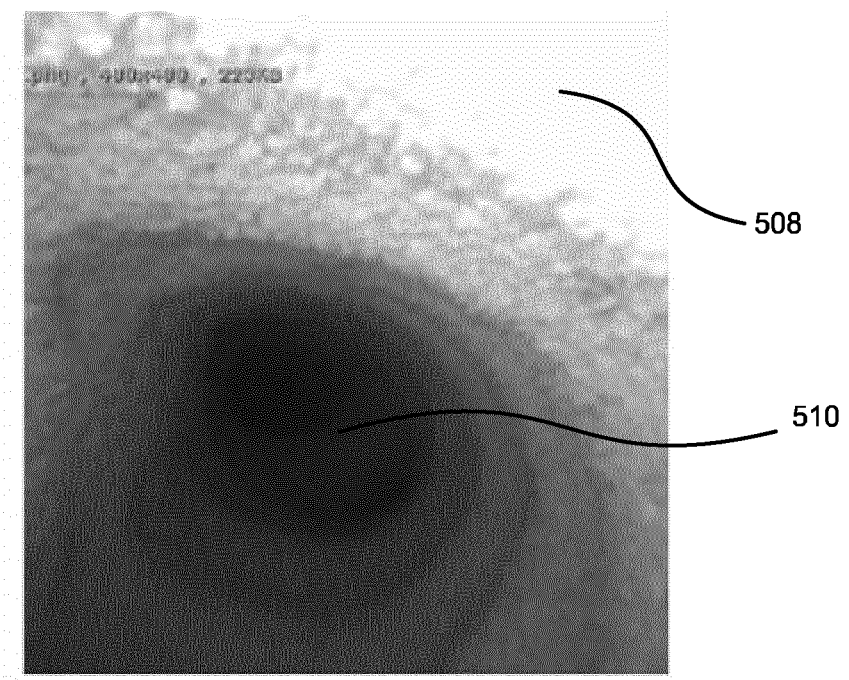
FIG. 5 illustrates an example of an image depicting an inside of the bronchial tube captured by the endoscope.

FIG. 5 illustrates an example of an image captured from a human bronchial tube that clearly illustrates the effects presented in relation to FIG. 4. An outer area 508 of the image, corresponding to the close lying area 408 illustrated in FIG. 4, is overexposed, in particular an upper right corner, and a central area 510, corresponding to the faraway lying area 410 illustrated in FIG. 4, is underexposed. An effect of having the overexposed and underexposed areas is that the operator will not be able to analyze parts of the bronchial tube corresponding to these areas.

Figure 6:
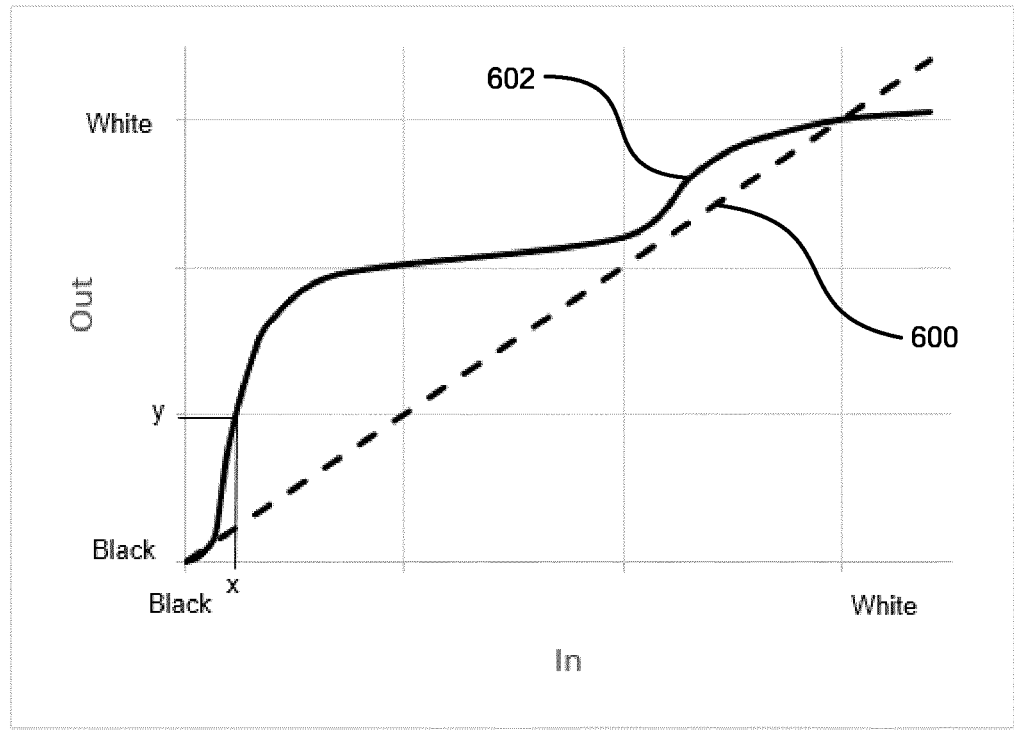
FIG. 6 illustrates an example of a gamma correction model, which in turn is an example of a non-linear scaling model according to the invention.

In order to compensate for a shape and light reflecting properties of a body cavity, such as a bronchial tube as illustrated by way of example in FIGS. 4 and 5, a non-linear gamma correction model may be used, as illustrated by way of example in FIG. 6.

As illustrated in FIG. 4, saturation of pixels is typically an issue on the image part showing a proximal wall in a channel (in which the endoscope is operated) being close to the tip part of the endoscope. Such regions tend to be over-exposed. Not being able to see darker details is an issue when looking deeper into the distal end of the channel, i.e. regions further away from the tip of the endoscope and thereby further away from the light source.

This problem may be solved by implementing the following method. When grabbing the image data, e.g. under conditions as illustrated in FIG. 4, the sensitivity of the pixels is adjusted to a level where saturation of pixels is unlikely to happen, even in image parts with high light intensity. This adjustment can be performed by setting exposure time and gain (sensitivity) of the pixels of the image data.

This will have the result that the pixels in parts of the image where the light intensity is low will be even darker, and details in these parts will not be discernible by the user when looking at the image as such. However, information on the details in these parts will still be present, and by making a non-linear scaling, such as the non-linear gamma correction shown in FIG. 6, it is possible to process the image such that details in both light parts and in dark parts can be discernible to the user.

The non-linear scaling can be described with reference to FIG. 6, showing how a scaling can be performed from an original (In) image to a scaled (Out) image.

In a simple example, the pixels could be scaled one by one i.e. a pixel having a value x in the In image will obtain the value y in the Out image. As indicated towards the black end of the In axis in FIG. 6, a small change in x will cause a considerable larger change in y due to the steep slope of the curve in darker regions. This will both cause an increased contrast in the darker regions, and it will lift the level of the dark regions, i.e. these regions will get a higher light intensity.

The straight dashed line 600 in FIG. 6 is a one to one scaling, which will not change the image at all. The curved line 602 will, as mentioned, increase the contrast in the dark parts of the image considerably, and make information in the darkest regions visible to the user. At the same time, the contrast in regions having an intermediate light intensity is reduced because of the relatively flat slope of the curve. This has the purpose of not making the regions already being relatively light, too light for the user to discern details in the image.

The effect of this non-linear contrast scaling is that the output image preferably should look as if a light source illuminates both the regions close to the endoscope tip and the regions further away from the endoscope tip with the same light intensity.

The exact shape of the curve will decide how the image will be scaled. In practice, curves of slightly different shapes will be provided, and the user will have the option to select between different options in the user interface, resulting in the use of one of these curves. Alternatively, the selection of curve could be made automatically, e.g. based on initial analysis of images from the body cavity being examined.

Figure 7A:
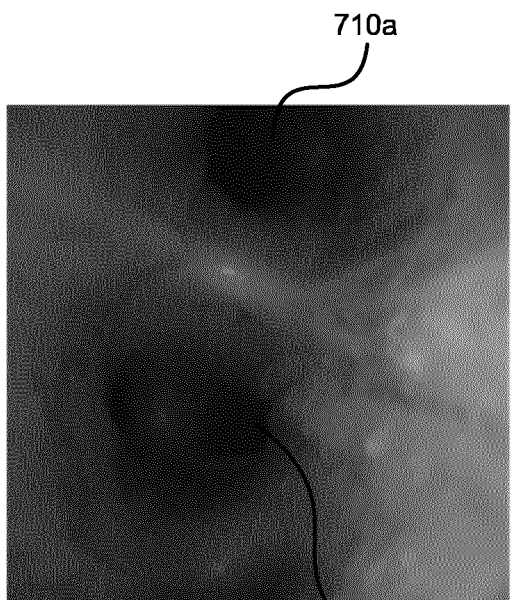
FIG. 7a illustrates an example of image data before applying the gamma correction model of FIG. 6.
Figure 7B:
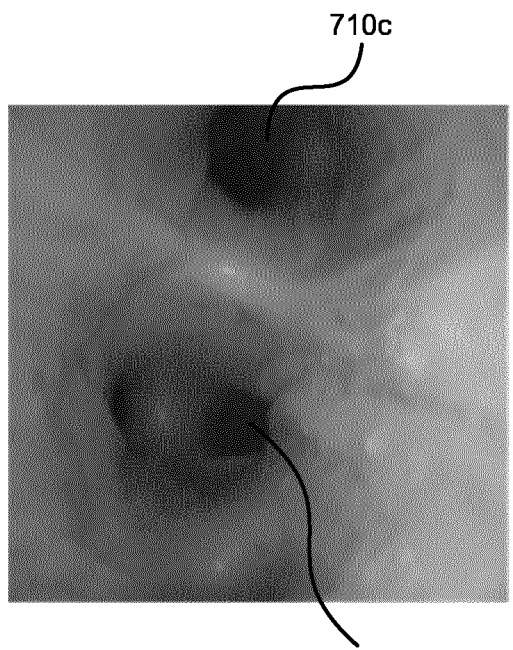
FIG. 7b illustrates an example of image data after applying the gamma correction model of FIG. 6.

FIGS. 7a and 7b illustrates by way of example images depicting a bronchial tube before and after the gamma correction model illustrated in FIG. 6 has been applied. In FIG. 7a, illustrating before the gamma correction model has been applied, central portions 710a, 710b of the image, i.e. parts of the bronchial tube lying relatively far away from the camera sensor, which corresponds to the second area 410 in FIG. 4, are dark and hence difficult for the operator to analyze. In FIG. 7b, after the gamma correction model has been applied, these central portions 710c, 710d are less dark, which has the positive effect that these can easily be analyzed.

Different body cavities are shaped in different ways. Thus, by having different gamma correction models for different body cavities, the image data can easily be transformed such that the operator more easily can analyze this and make relevant conclusions based upon it. For instance, the gamma correction model illustrated in FIG. 6 may be used for image data captured in human body bronchial tubes. Which body cavity that is being examined may be provided as user input via e.g. the monitor, but it may also be automatically detected by the endoscope and/or the monitor itself e.g. by analyzing image data obtained by the image capturing device.

Transforming the image data by applying the non-linear gamma correction model requires data processing capability. Since the endoscope may be a single-use piece of equipment in order to assure that the risk of cross-contamination between patients is eliminated, image data processing operations, such as applying the gamma correction model, may advantageously be performed in the monitor, which is a re-usable piece of equipment, in order to keep a total cost of operation low.

Figure 8:
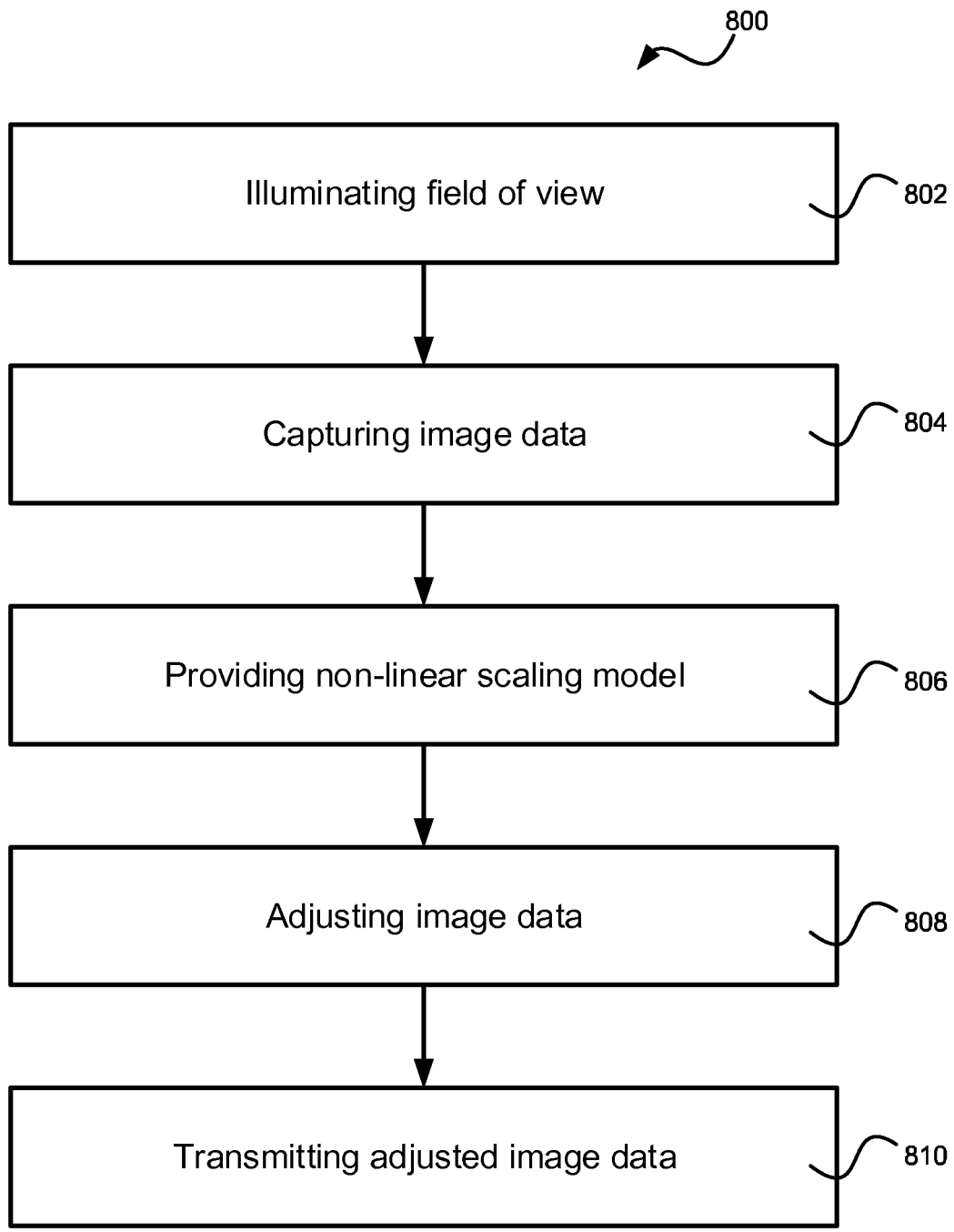
FIG. 8 is a flowchart illustrating steps of a method for processing image data before presenting on the monitor.

FIG. 8 generally illustrates a flowchart 800 illustrating a method for processing image data by using a medical visual aid system comprising an endoscope and a monitor. The endoscope is, as the endoscope illustrated in FIGS. 1 and 4, configured to be inserted into a body cavity and comprises an image capturing device and a light emitting device, and the monitor is configured for presenting image data, as the monitor illustrated in FIG. 2. The method comprises four main steps.

In a first step 802 a field of view of the image capturing device is illuminated with the light emitting device.

In a second step 804, image data is captured using the image capturing device.

In a third step 806, a non-linear scaling model adapted to the body cavity is provided.

In a fourth step 808, the image data is adjusted by applying the non-linear scaling model such that adjusted image data is formed.

Again referring to FIG. 1, in order to reduce an impact of noise in the image data transmitted from the image sensor it is known to shield the insertion tube cable placed inside the insertion tube 102 and the connection cable 114, in use provided between the endoscope 100 and the monitor 200. By doing so, a risk of having the image data affected by signals from else-where can be reduced, which result in that there is less noise in the image data received by the monitor 200.

A disadvantage with shielding the insertion tube cable and the connection cable is however increased production cost, and also since additional material is needed an increased environmental cost. This is more relevant for single-use endoscopes than for other equipment made to be used multiple times.

Another disadvantage is that by having the insertion tube cable shielded a flexibility of the insertion tube 102 may be decreased, which may show in that additional energy is needed for operating the bending section 106 and/or that a range of the bending section 106 is limited due to the shielding.

Since at least a part of the noise is periodic noise or, in other words, fixed pattern noise, it is instead of shielding the insertion tube cable and/or the connection cable 114 a possibility to have the insertion tube cable and/or the connection cable 114 unshielded, or provided with a reduced shielding, and to de-noise the image data in the monitor 200 in order to remove, or at least reduce, the noise in the image data.

If the image sensor is read out line by line at regular intervals, the periodic noise, for instance caused by the clock frequency, will be present in the image data with a regularity, which may show in that there is more noise in a first direction than in a second direction. For instance, the image data, which may be represented as a matrix with rows and columns, may have a stronger presence of noise in a horizontal direction, i.e. column noise, than in a vertical direction, i.e. row noise.

Thus, in order to provide a cost efficient single-use endoscope with improved flexibility it is possible to make use of a method for de-noising the image data as presented below.

A method for de-noising image data comprising first directional noise in a first direction and second directional noise in a second direction, wherein the first directional noise is greater than the second directional noise, said method comprising receiving the image data, comprising first pixels in the first direction and second pixels in the second direction, from the image sensor provided in the tip part 108 of the endoscope 100, and performing a convolution between the image data and a direction biased periodic noise compensation kernel, wherein the direction biased periodic noise compensation kernel is a convolution between an averaging kernel and a sharpening kernel, wherein the direction biased periodic noise compensation kernel is providing equal averaging of the image data in the first direction and the second direction, and providing sharpening in the second direction.

The direction biased periodic noise compensation kernel may provide sharpening in the second direction solely.

The first direction and the second direction may be perpendicular.

The endoscope 100 may comprise an insertion tube cable connected to the image sensor, wherein the insertion tube cable may be unshielded.

The endoscope 100 may comprise a connection cable 114 connected to the insertion tube cable, wherein the connection cable may be unshielded.

The step of performing the convolution between the image data and the direction biased periodic noise compensation kernel may be made in the monitor 200 connected to the endoscope 100.

The direction biased periodic noise compensation kernel may be:

| -⅓ | -⅓ | -⅓ |
|---|---|---|
| 1 | 1 | 1 |
| -⅓ | -⅓ | -⅓ |

The averaging kernel may be:

| ⅑ | ⅑ | ⅑ |
|---|---|---|
| ⅑ | ⅑ | ⅑ |
| ⅑ | ⅑ | ⅑ |

The sharpening kernel may be:

| -1 | -1 | -1 |
|---|---|---|
| -1 | 9 | -1 |
| -1 | -1 | -1 |

The invention has mainly been described above with reference to a few embodiments. However, as is readily appreciated by a person skilled in the art, other embodiments than the ones disclosed above are equally possible within the scope of the invention, as defined by the appended patent claims.

What is claimed is:

1. A method for processing image data obtained using a medical visual aid system comprising an endoscope and a monitor, wherein the endoscope is configured to be inserted into a body cavity and comprises an image capturing device for capturing image data and a light emitting device, said method comprising:
    by the monitor:
    setting exposure settings to generate darkened image data from the image capturing device, the darkened image data including darker pixel areas and lighter pixel areas, the darker pixel areas being darker than the lighter pixel areas;
    receiving the darkened image data from the endoscope;
    accessing a non-linear intensity scaling model configured to change intensities of the pixels in the darker pixel areas more than intensities of the pixels in the lighter pixel areas;
    applying the non-linear intensity scaling model to the darkened image data to form adjusted image data; and
    presenting the adjusted image data,
    wherein the darkened image data includes a low intensity image data sub-set, and a high intensity image data sub-set, wherein the low intensity image data sub-set comprises pixels having intensity levels up to 25% of a maximum intensity, and wherein the high intensity image data sub-set comprises pixels having intensity levels from 95% of the maximum intensity, wherein the non-linear intensity scaling model is configured to increase the intensities of the pixels forming the low intensity image data sub-set and to decrease the intensities of the pixels forming the high intensity image data sub-set.

2. The method according to claim 1, wherein the exposure settings are configured such that no more than a single pixel is saturated by light.

3. The method according to claim 1, wherein the exposure settings are configured to emphasize a central part of a field of view of the image capturing device.

4. The method according to claim 1, wherein the non-linear intensity scaling model is also adapted to the monitor.

5. The method according to claim 1, wherein the non-linear intensity scaling model is also adapted to the light emitting device.

6. The method according to claim 1, wherein the non-linear intensity scaling model is configured to increase the contrast in the dark parts of the darkened image data and reduce the contrast in the parts of the image data having an intermediate light intensity in a manner whereby pixels having low pixel intensity values are scaled up significantly and pixels having mid-range pixel intensity values are only slightly adjusted or not adjusted at all.

7. The method according to claim 6, wherein the non-linear intensity scaling model is a scaling function mapping input intensities to output intensities.

8. The method according to claim 7, wherein the scaling function includes a bend.

9. The method according to claim 8, wherein the scaling function has a first part, the first part being followed by a second part, the second part being followed by a third part, and wherein the average slope of the second part is lower than the average slope of the first part and the average slope of the third part.

10. The method according to claim 1, wherein the darkened image data includes an intermediate intensity image data sub-set, wherein the non-linear intensity scaling model is set to increase intensity of the low intensity image data sub-set by a first increase factor and to increase intensity of the intermediate intensity image data sub-set by a second increase factor, wherein the first increase factor is greater than the second increase factor.

11. The method according claim 1, wherein accessing a non-linear intensity scaling model comprises:
    determining a body cavity type to which the body cavity is related, and
    selecting the non-linear intensity scaling model based on the body cavity type.

12. The method of claim 1, wherein the monitor has stored therein a plurality of non-linear intensity scaling models, and accessing a non-linear intensity scaling model comprises receiving, with a user interface, a selection by a user of the non-linear intensity scaling model from the plurality of non-linear intensity scaling models.

13. The method of claim 1, further comprising, by the endoscope:
    generating the darkened image data by reducing an exposure in the image capturing device based on the exposure settings set by the monitor.

14. The method of claim 13, wherein the exposure settings are based on an evaluation of preceding image data.

15. A medical visual aid system comprising a monitor, the monitor comprising:
    an image data processing device for adjusting image data generated by an endoscope, the processing including applying a non-linear scaling model adapted to a body cavity such that adjusted image data is formed; and
    a display device for presenting the adjusted image data;
    wherein the non-linear scaling model is a non-linear intensity scaling model, and
    wherein the image data processing device for adjusting the image data by applying a non-linear scaling model is configured to increase intensity of a low intensity image data sub-set, wherein the low intensity image data sub-set comprises intensity levels up to 25% of maximum intensity, and decrease intensity of a high intensity image data sub-set, wherein the high intensity image data sub-set comprises intensity levels from 95% of the maximum intensity.

16. The medical visual aid system according to claim 15, wherein exposure settings of the image data processing device are configured to emphasize on a central part of a field of view of the image capturing device.

17. The medical visual aid system according to claim 15, wherein the non-linear scaling model is also adapted to the light emitting device.

18. The medical visual aid system according to claim 15, wherein the non-linear scaling model is a non-linear intensity scaling model.

19. The medical visual aid system according to claim 18, wherein the non-linear intensity scaling model is configured to, in the image presented on the display device, increase the contrast in the dark parts of the image and reduce the contrast in the parts of the image having an intermediate light intensity in a manner whereby pixels having low pixel intensity values are scaled up significantly and pixels having mid-range pixel intensity values are only slightly adjusted or not adjusted at all.

20. The medical visual aid system according to claim 19, wherein the non-linear intensity scaling model is a scaling function mapping input intensities to output intensities.

21. The medical visual aid system according to claim 20, wherein the scaling function is provided with a bend.

22. The medical visual aid system according to claim 21, wherein the scaling function has a first part, the first part being followed by a second part, the second part being followed by a third part, and wherein the average slope of the second part is lower than the average slope of the first part and the average slope of the third part.

23. The medical visual aid system according to claim 15, wherein the non-linear scaling model is set to increase intensity of the low intensity image data sub-set by a first increase factor, wherein the first increase factor is greater than the increase factors used for other sub-sets of the image data.

24. The medical visual aid system according to claim 15, wherein the image data processing device is further configured to determine a body cavity type to which the body cavity is related, and select the non-linear scaling model based on the body cavity type.

25. The medical visual aid system according to claim 15, further comprising the endoscope, wherein the endoscope is configured to be inserted into the body cavity and generate the image data, and wherein the endoscope comprises a light emitting device and an image capturing device.

26. A computer program comprising computer program code adapted to perform a method when said computer program is run on a computer, said method comprising:
receiving image data corresponding to a body cavity from an endoscope, the image data including saturated pixels and unsaturated pixels;
setting exposure settings to generate darkened image data from the image data, the darkened image data including darker pixel areas and lighter pixel areas, the darker pixel areas being darker than the lighter pixel areas;
accessing a non-linear intensity scaling model configured to change intensities of the pixels in the darker pixel areas more than intensities of the pixels in the lighter pixel areas;
applying the non-linear intensity scaling model to the darkened image data to form adjusted image data; and
outputting the adjusted image data,
wherein the darkened image data includes a low intensity image data sub-set, and a high intensity image data sub-set, wherein the low intensity image data sub-set comprises pixels having intensity levels up to 25% of a maximum intensity, and wherein the high intensity image data sub-set comprises pixels having intensity levels from 95% of the maximum intensity, wherein the non-linear intensity scaling model is configured to increase the intensities of the pixels forming the low intensity image data sub-set and to decrease the intensities of the pixels forming the high intensity image data sub-set.

* * * * *